US012567496B2

(12) United States Patent
Arrowsmith et al.

(10) Patent No.: US 12,567,496 B2
(45) Date of Patent: Mar. 3, 2026

(54) METHOD AND APPARATUS FOR DISPLAYING AND ANALYZING MEDICAL SCAN IMAGES

(71) Applicant: Optellum Limited, Oxford (GB)

(72) Inventors: David Arrowsmith, Oxford (GB); Quentin Chometon, Oxford (GB); Timor Kadir, Oxford (GB)

(73) Assignee: Optellum Limited, Oxford (GB)

( * ) Notice: Subject to any disclaimer, the term of this patent is extended or adjusted under 35 U.S.C. 154(b) by 643 days.

(21) Appl. No.: 18/077,540

(22) Filed: Dec. 8, 2022

(65) Prior Publication Data

US 2024/0194323 A1 Jun. 13, 2024

(51) Int. Cl.
*G16H 30/20* (2018.01)
*G06T 7/00* (2017.01)
*G16H 30/40* (2018.01)

(52) U.S. Cl.
CPC ........... *G16H 30/20* (2018.01); *G06T 7/0012* (2013.01); *G16H 30/40* (2018.01)

(58) Field of Classification Search
CPC ....... G16H 30/20; G16H 30/40; G06T 7/0012
See application file for complete search history.

(56) References Cited

U.S. PATENT DOCUMENTS

| | | | |
|---|---|---|---|
| 8,732,601 B2 | 5/2014 | Licato | |
| 10,297,352 B2 | 5/2019 | Sakagawa et al. | |
| 10,803,579 B2 | 10/2020 | Song et al. | |

| | | | |
|---|---|---|---|
| 2003/0095692 A1* | 5/2003 | Mundy | G06T 7/0012 |
| | | | 382/128 |
| 2018/0341751 A1 | 11/2018 | Lyman | |
| 2020/0118164 A1* | 4/2020 | DeFrank | G06Q 30/0269 |
| 2021/0090694 A1* | 3/2021 | Colley | G16B 30/00 |
| 2023/0051982 A1* | 2/2023 | Sasidharan | G16H 15/00 |
| 2023/0197248 A1* | 6/2023 | Cambray Roma | G16H 50/50 |
| | | | 705/2 |
| 2023/0274809 A1* | 8/2023 | Dimitrova | G06F 8/34 |
| | | | 705/3 |

(Continued)

OTHER PUBLICATIONS

An Appraisal of Nodule Diagnosis for Lung Cancer in CT Images. Zhang G et al. Journal of Medical Systems (2019) 43: 181. https://doi.org/10.1007/s10916-019-1327-0.

(Continued)

*Primary Examiner* — Mohammed H Zuberi
(74) *Attorney, Agent, or Firm* — Optimus Patents US, LLC

(57) ABSTRACT

A display system for a computer aided lung cancer diagnosis system is described. The system comprises: a user interface which comprises: a patient information display wherein the patient information comprises one or more of: patient name, patient age, patient sex, smoking history, disease history, and current patient status; an image display for displaying at least one of a selected plurality of medical images acquired at different times and an associated image report; and a patient timeline display for providing a visual display of patient events over a set time period; and a proxy data store to store the selected plurality of medical images, wherein the selected plurality of medical images are provided from an external archive and are pre-selected to comprise one or more relevant archive images, and exclude irrelevant archive images.

16 Claims, 8 Drawing Sheets

(56)                References Cited

U.S. PATENT DOCUMENTS

2023/0367784 A1* 11/2023 Jacobs ................... G16H 50/70
2023/0410223 A1* 12/2023 Dobson ................. G16H 15/00

OTHER PUBLICATIONS

The IASLC Lung Cancer Staging Project: Proposals for Revision of the TNM Stage Groupings in the Forthcoming (Eighth) Edition of the TNM Classification for Lung Cancer. Peter Goldstraw et al. Journal of Thoracic Oncology vol. 11 No. 1: 39-51; 2016.
Reduced lung-cancer mortality with low-dose computed tomographic screening. Aberle DR, et al. N Engl J Med. 2011;365(5):395-409. Epub Jul. 1, 2011. PubMed PMID: 21714641.
Nelson Study Shows CT Screening for Nodule Volume Management Reduces Lung Cancer Mortality by 26 Percent in Men. Koning HJD. Toronto, Canada: IASLC; 2018.
Recent Trends in the Identification of Incidental Pulmonary Nodules. Michael K. Gould et al. American Journal of Respiratory and Critical Care Medicine vol. 192 No. 10; 2015.
British Thoracic Society guidelines for the investigation and management of pulmonary nodules. Callister ME et al; British Thoracic Society Pulmonary Nodule Guideline Development Group; British Thoracic Society Standards of Care Committee. 2015. Thorax. Aug. 2015;70 Suppl 2:ii1-ii54. doi: 10.1136/thoraxjnl-2015-207168. https://doi.org/10.1136/thoraxjnl-2015-207168.
Guidelines for management of incidental pulmonary nodules detected on CT images: from the Fleischner Society 2017. MacMahon, Heber, et al. Radiology 284.1 (2017): 228-243.
Evaluation of individuals with pulmonary nodules: when is it lung cancer? Diagnosis and management of lung cancer, 3rd ed. Gould MK et al. American College of Chest Physicians evidence-based clinical practice guidelines. Chest. 368 2013;143(5 Suppl):e93S-e120S. Epub May 10, 2013. doi: 10.1378/chest.12-2351. PubMed PMID: 369 23649456; PubMed Central PMCID: PMCPMC3749714.
Development of a Risk Prediction Model to Estimate the Probability of Malignancy in Pulmonary Nodules Being Considered for Biopsy. Reid M, et al. Chest. 2019;156(2):367-75. Epub Apr. 4, 2019. doi: 10.1016/j.chest.2019.01.038. PubMed PMID: 417 30940455.
Invasive modalities for the diagnosis of peripheral lung nodules. Expert Review of Respiratory Medicine. Kalanjeri S et al. 2021 https://doi.org/10.1080/17476348.2021.1913059.
Pneumothorax after transthoracic needle biopsy of lung lesions under CT guidance. Boskovic T et al. Journal of thoracic disease, 6 Suppl 1(Suppl 1), S99-S107. https://doi.org/10.3978/j.issn.2072-1439.2013.12.08 (2014).
No stone unturned: Nodule Net, an intervention to reduce loss to follow-up of lung nodules. Weinstock TG et al. Respiratory Medicine 157 (2019) 49-51. https://doi.org/10.1016/j.rmed.2019.09.003.
Nodule net: A prospective safety net program to reduce loss to follow-up and increase early detection of lung cancer. Harpreet Singh et al. DOI: 10.1200/JCO.2021.39.15_suppl. 1564 Journal of Clinical Oncology 39, No. 15_suppl (May 20, 2021) 1564-1564.

* cited by examiner

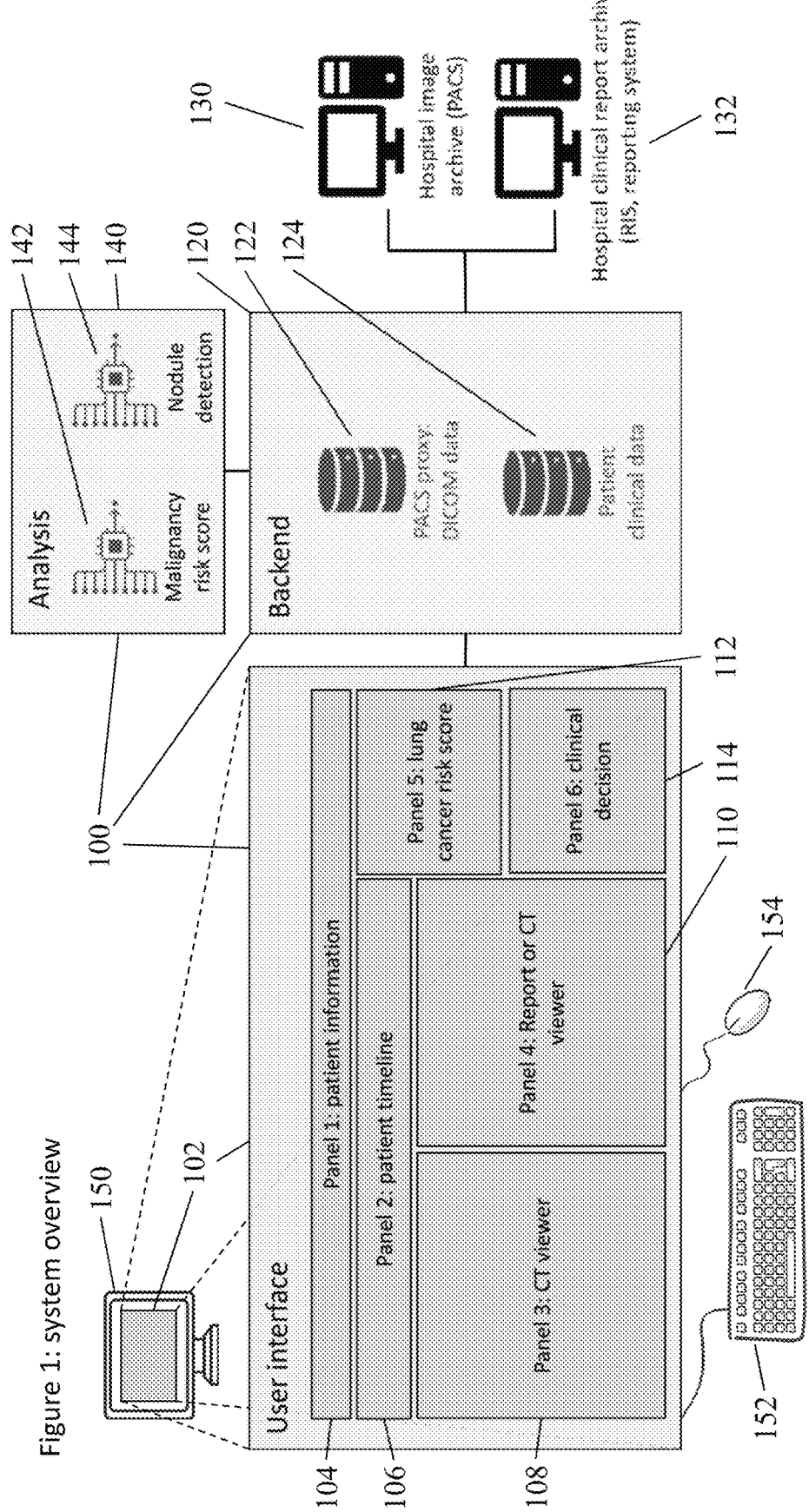
Figure 1: system overview

Figure 2a: Patient information panel example – full
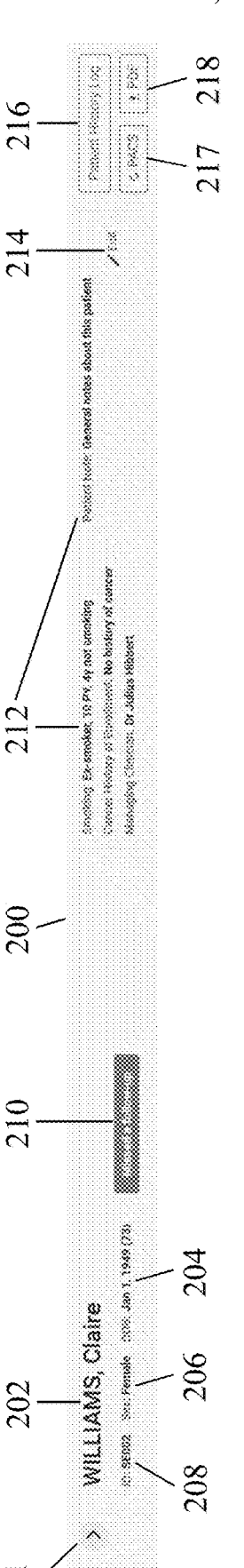
Figure 2b: Patient information panel example – essential
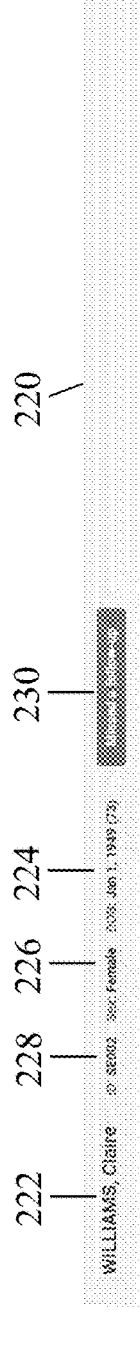
Figure 2c: Patient status examples
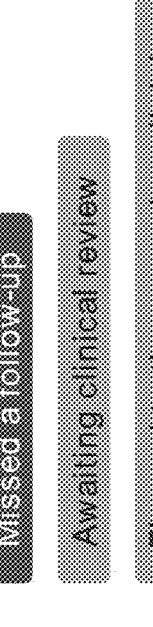

Figure 3a: Timeline panel example

Figure 3b: Timeline panel example – displaying archived study

Figure 4: Medical image and report example
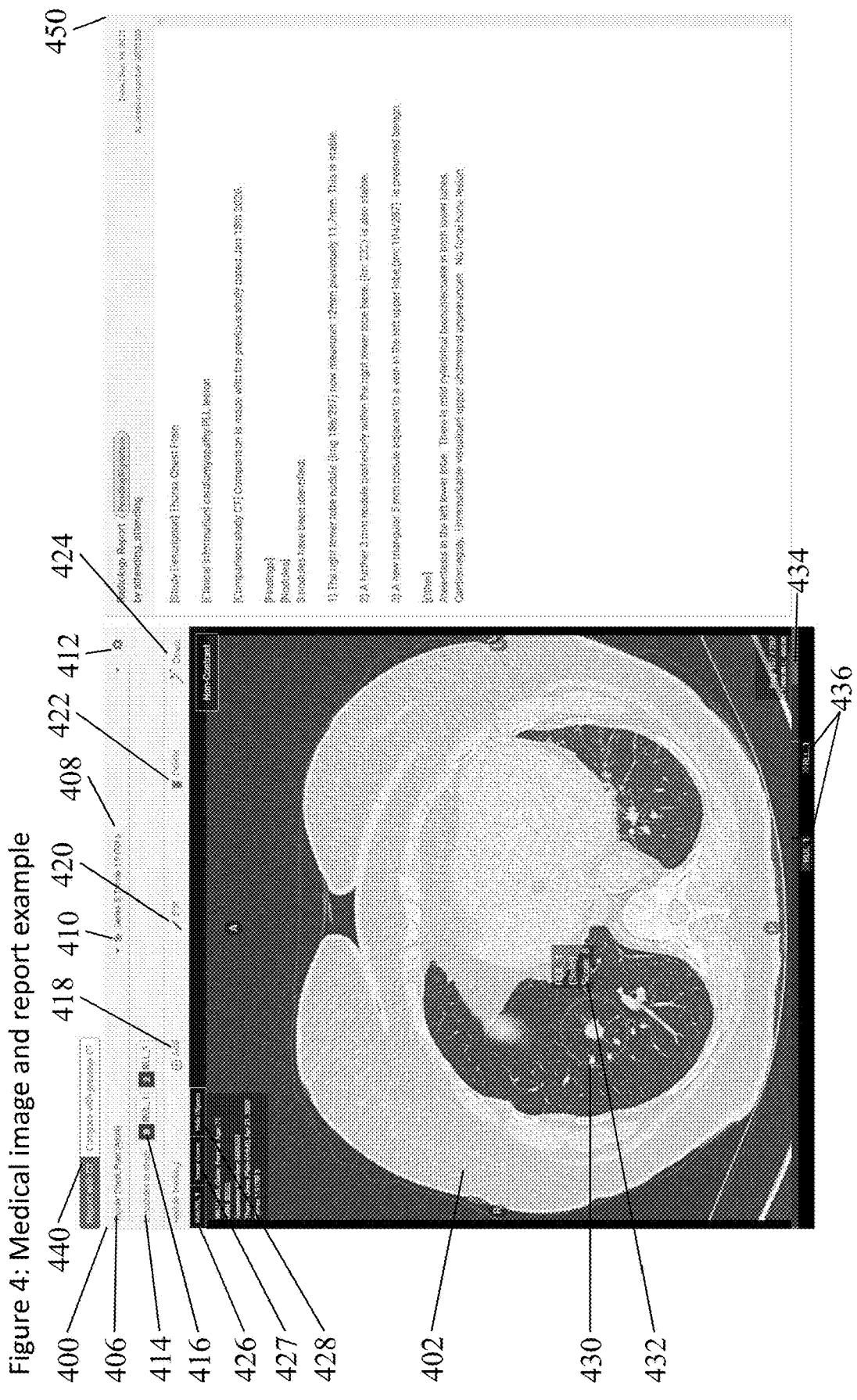

Figure 5: Medical images over time example
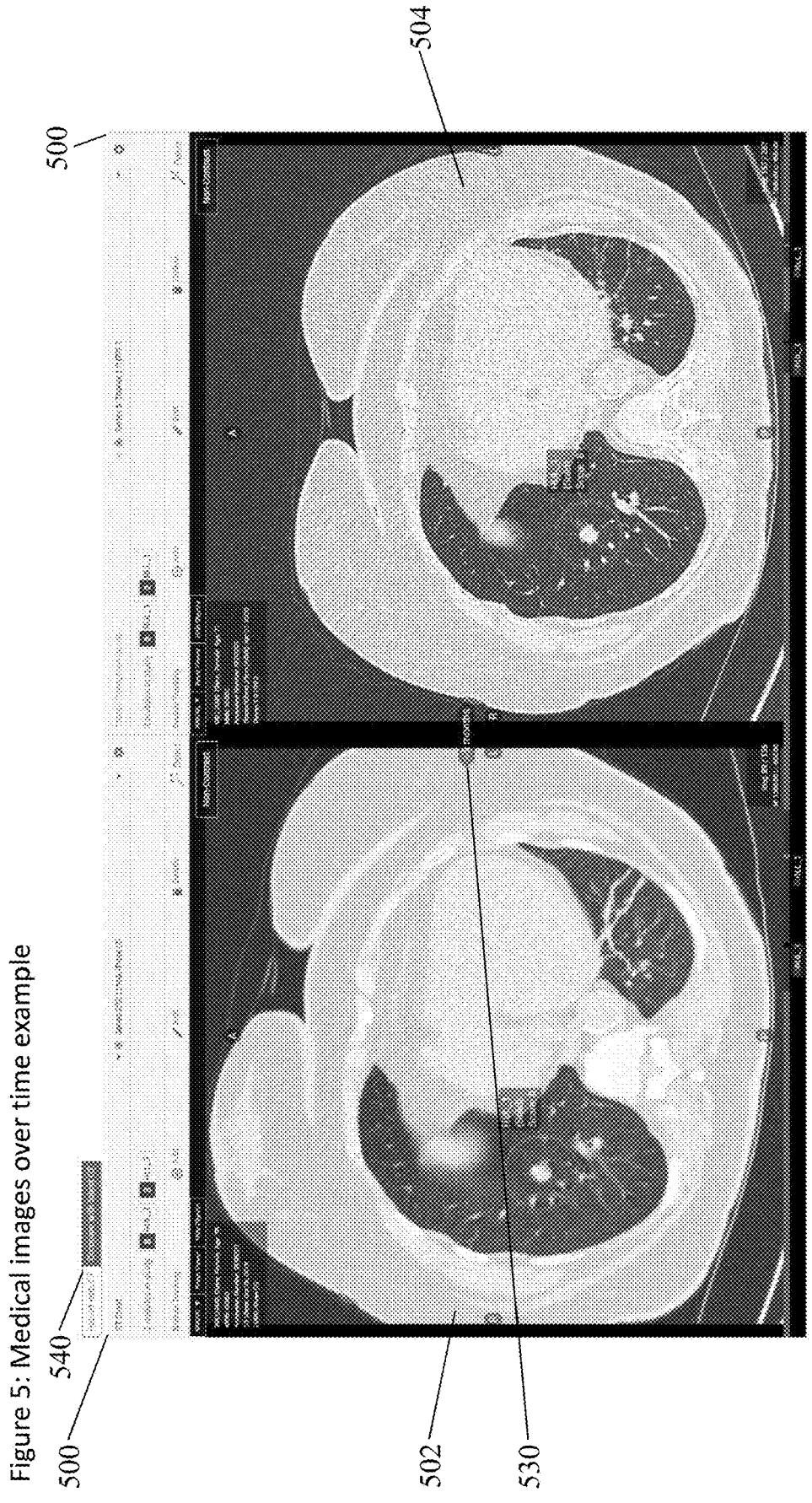

Figure 6b: Actions unit
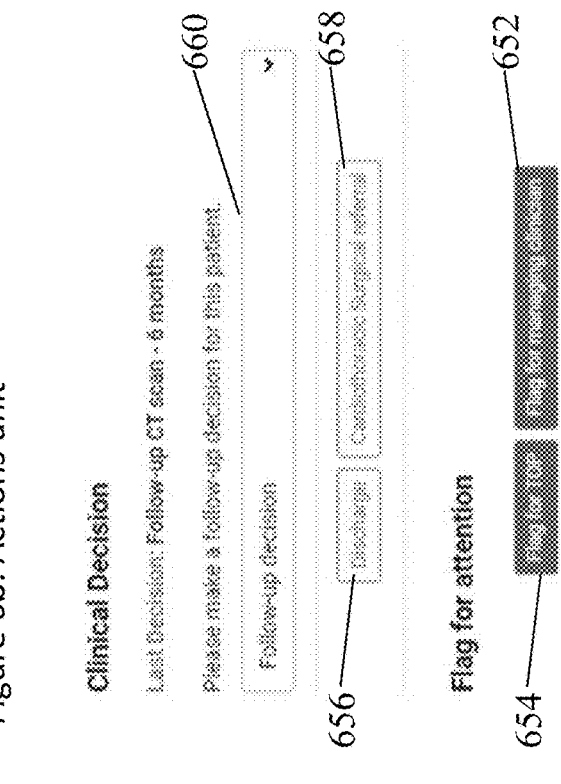
Figure 6a: Lung cancer risk score unit
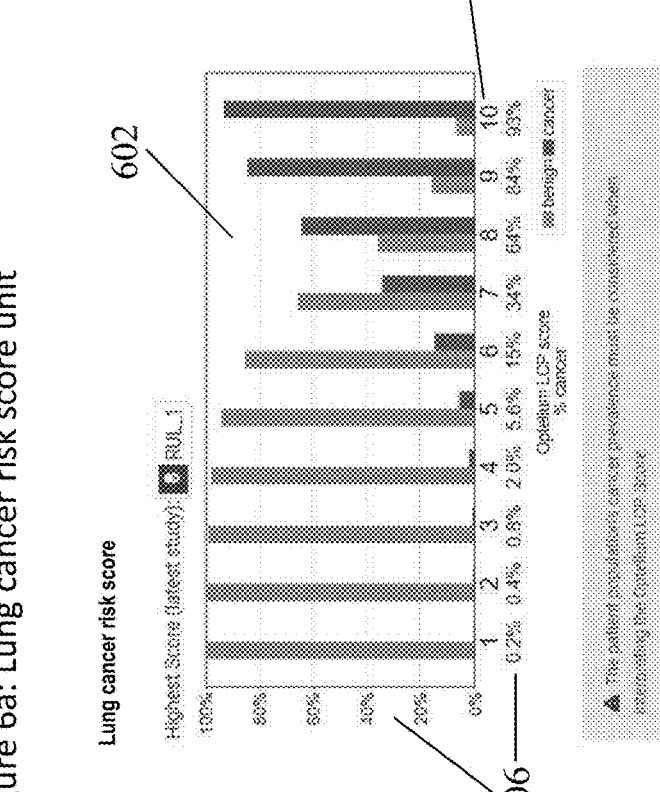

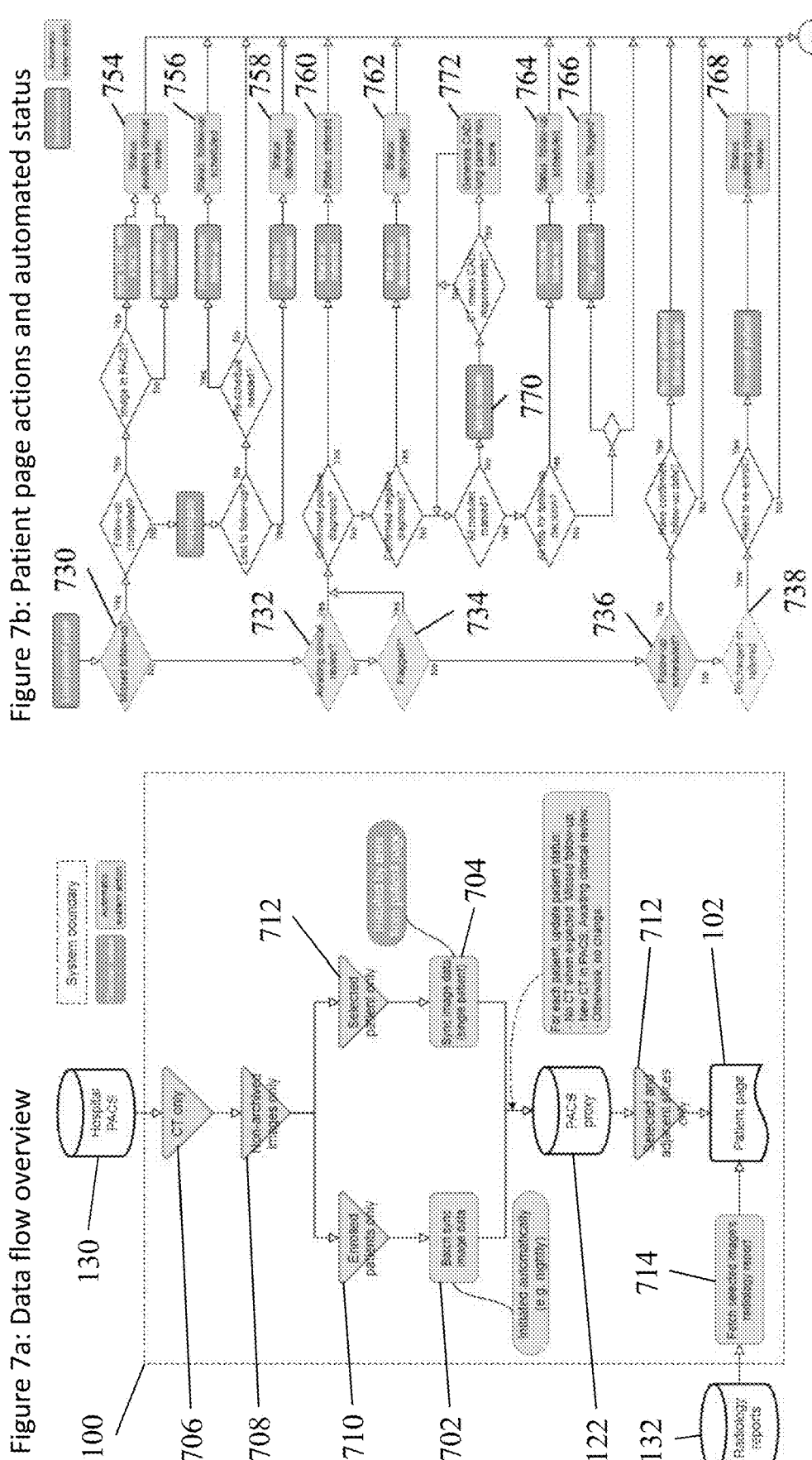
Figure 7b: Patient page actions and automated status
Figure 7a: Data flow overview

METHOD AND APPARATUS FOR DISPLAYING AND ANALYZING MEDICAL SCAN IMAGES

This invention relates to a method and apparatus to display medical scan images that are provided from an external archive. This can be used to assist clinicians in assessing malignancy of lung nodules and managing patients through lung nodule clinics.

FIELD OF INVENTION

This invention relates to the field of computer aided detection and diagnosis systems that are preferably used for the management of the diagnosis of patients with suspected cancer, specifically, patients with lung nodules whose malignancy diagnosis is unknown (indeterminate pulmonary nodules). The invention includes a system of tools for such management, including automated methods for assisting clinicians in the interpretation of medical images, with the aim of shortening the time to confirmed diagnosis, reducing exposure of patients to unnecessary invasive procedures, and reducing loss to follow-up, when compared to current practice.

BACKGROUND OF INVENTION

Lung cancer is a deadly disease that has significantly better survival rates when identified early, because patients stand a much better chance of therapeutic success in the earlier stages: 5-year survival rate is 10-20% for all lung cancer overall, but over 70% for early-stage disease detection [e.g. refs. 1, 2].

There are two principal mechanisms by which lung cancer may be diagnosed at an early stage. The first is through screening, using computed tomography (CT), specifically low-dose CT, which was shown to reduce lung cancer deaths by 20% in the USA [3], and by 26% in Europe [4].

The second mechanism is detection as an incidental finding in patients undergoing imaging for unrelated reasons [5]. For example, chest CT scans are performed as part of a whole-body examination after a car accident, or as part of a cardiac CT scan in a series of investigations for cough or shortness of breath. Any such imaging studies may result in the scan demonstrating a pulmonary nodule.

Pulmonary nodules are approximately rounded structures that appear on imaging as focal opacities, and by traditional definition are up to 30 mm in diameter. They are commonly detected: for example, in populations at high risk of lung cancer, nodules are found in 20-50% of individuals taking part in screening programmes [6]. Most detected lung nodules are benign, with the prevalence of lung cancer being as low as 5% among populations of individuals having lung nodules over 5 mm [6, 8].

Lung nodules that are not clearly benign or malignant are termed "indeterminate" and these pose a significant challenge to clinicians. Histological examination of tissue acquired by biopsy or surgical resection is required for a diagnosis of malignancy, while benign status can also be confirmed by nodule stability on follow-up imaging over time, or resolution [9]. Each of these options carries risk: for example, CT-guided biopsy has significant risks of complications such as lung collapse (pneumothorax) [10], the reported rates of which vary widely, averaging at around 20% [11]. So follow-up CT imaging from 3 to 24 months is commonly preferred, which, in the case of malignancy could mean delay to therapeutic management.

Current clinical guidelines [e.g. 6, 7, 8] suggest that clinicians recommend follow-up diagnostic steps based on available information such as patient background (e.g. age, sex, smoking history, cancer history), and the appearance, size and growth of pulmonary nodules in various medical imaging modalities, primarily CT. Imaging reporting is still mainly done by the clinician, although increasingly, there are devices which help clinicians in this task, for example by automating detection and classification of anatomical features in the image.

Computer aided detection (CADe) devices serve to assist clinicians in assessing the medical images. CADe devices need to provide a clinician with standardized, objective and repeatable information. The information typically relates to particular anatomical regions, including both normal tissue and lesions, within a person. CADe devices may be used as a so-called second reader device, which is based on an approach whereby a radiologist first looks at an image resulting from a scan, for example a mammogram. The radiologist will then, based on training and experience, identify areas of the scan where the radiologist considers that there may need to be a further investigation, for example a biopsy. However, the radiologist can then consider the CADe findings, so the CADe device is performing a second look at the scan, with the aim of reducing false negatives (missed findings).

Computer aided diagnosis (CADx) devices are a related technology to CADe. CADx devices attempt to solve a different problem and relate generally to risk assessment. Instead of focussing on potentially missed findings as in CADe, they try to assist the user to classify findings correctly, for instance, either as malignant or benign in the case of potentially cancerous lesions. They rely on the user to identify abnormalities, and typically provide a score that is indicative of the risk of malignancy. Examples of commercial CADx devices include the breast cancer screening product 'Transpara™' from 'Screenpoint™'. There are many non-clinical CADx devices in the academic literature.

In the space of lung cancer, CADx devices have traditionally focused on evaluating lung nodules to produce malignancy risk scores, with the aim of helping clinicians make more appropriate decisions for the patient. Examples of such lung cancer CADx devices include qCT-Lung from qure.ai. The connection between risk assessment and clinical decision-making lies in that the most appropriate next step for a given patient with a lung nodule depends on the risk of it being malignant. For example, higher risk cases would warrant shorter term actions (e.g., PET/CT, biopsy, or short-term CT follow-up), while lower risk cases can be addressed with longer term CT follow-ups. The consensus of experts on how to link risk and clinical decision is collected in clinical guidelines published regularly by the relevant medical societies. In the case of lung cancer, these guidelines include those from the British Thoracic Society [6] and the Fleischner Society [7]. In these guidelines, risk assessment of the lung nodule is central to the decision-making process, hence it is thought that CADx devices that help clinicians better assess risk can lead to better management.

However, it remains a challenge for clinicians to have all the necessary and relevant information easily to hand. Patients with conditions unrelated to lung cancer may have many imaging studies performed, but only a small proportion of these are useful for diagnosis of lung nodules, resulting in inefficiencies in finding these images, and making viewing lung nodules' progress over time difficult. PACS and reporting software are separate, and it may not be immediately clear which reports apply to which images. Other information relevant to lung cancer diagnosis, such as the patient's smoking history, may not be easily available to the clinician making follow-up decisions. Existing patient follow-up appointments may be recorded in yet another system, making tracking and prioritisation difficult. All these issues can be compounded when a patient's lung nodule has been detected by an investigation for an unrelated reason (incidentally detected nodules) where information may reside with a different specialty or different hospital.

Moreover, there is significant occurrence of loss to follow-up in the case of pulmonary nodules, meaning patients may not be diagnosed. Causes include high volume of imaging studies (including those unrelated to lungs), inadequate tracking systems or reminders, and especially in the case of incidentally detected findings, incomplete communication between disciplines [12]. Some attempts have been made to improve this, such as Nodule Net, which consists of centralised nurse navigator managing a follow-up database, with reminders to the primary care provider if follow-up was not completed, and referral for management where appropriate [13].

REFERENCES

1. An Appraisal of Nodule Diagnosis for Lung Cancer in CT Images. Zhang G et al. Journal of Medical Systems (2019) 43: 181. https://d 0.1097/10916-019-1327-0.
2. The IASLC Lung Cancer Staging Project: Proposals for Revision of the TNM Stage Groupings in the Forthcoming (Eighth) Edition of the TNM Classification for Lung Cancer. Peter Goldstraw et al. Journal of Thoracic Oncology Vol. 11 No. 1: 39-51; 2016.
3. Reduced lung-cancer mortality with low-dose computed tomographic screening. Aberle D R, et al. N Engl J Med. 2011; 365(5):395-409. Epub 2011/07/01. PubMed PMID: 21714641.
4. NELSON Study Shows CT Screening for Nodule Volume Management Reduces Lung Cancer Mortality by 26 Percent in Men. Koning H J D. Toronto, Canada: IASLC; 2018.
5. Recent Trends in the Identification of Incidental Pulmonary Nodules. Michael K. Gould et al. American Journal of Respiratory and Critical Care Medicine Volume 192 Number 10; 2015.
6. British Thoracic Society guidelines for the investigation and management of pulmonary nodules. Callister M E et al; British Thoracic Society Pulmonary Nodule Guideline Development Group; British Thoracic Society Standards of Care Committee. 2015. Thorax. 2015 Aug; 70 Suppl 2:ii1-ii54. doi: 10.1136/thoraxjnl-2015-207168. 2168. https://doi.org/10.1136/thoraxjnl-2015-207168
7. Guidelines for management of incidental pulmonary nodules detected on CT images: from the Fleischner Society 2017. MacMahon, Heber, et al. Radiology 284.1 (2017): 228-243.
8. Evaluation of individuals with pulmonary nodules: when is it lung cancer? Diagnosis and management of lung cancer, 3rd ed. Gould M K et al. American College of Chest Physicians evidence-based clinical practice guidelines. Chest. 368 2013; 143(5 Suppl):e93S-e120S. Epub 2013/05/10. doi: 10.1378/chest.12-2351. PubMed PMID: 369 23649456; PubMed Central PMCID: PMCPMC3749714.
9. Development of a Risk Prediction Model to Estimate the Probability of Malignancy in Pulmonary Nodules Being Considered for Biopsy. Reid M, et al. Chest. 2019; 156(2):367-75. Epub 2019/04/04. doi: 10.1016/j.chest.2019.01.038. PubMed PMID: 417 30940455.
10. Invasive modalities for the diagnosis of peripheral lung nodules. Expert Review of Respiratory Medicine. Kalanjeri S et al. 2021 https://doi.org/10.1080/17476348.2021.1913059.
11. Pneumothorax after transthoracic needle biopsy of lung lesions under CT guidance. Boskovic T et al. Journal of thoracic disease, 6 Suppl 1(Suppl 1), S99-S107. https://doi.org/10.3978/j.jssn.2072-1439.2013.12.08 (2014).
12. No stone unturned: Nodule Net, an intervention to reduce loss to follow-up of lung nodules. Weinstock T G et al. Respiratory Medicine 157 (2019) 49-51. https://doi.org/10.1016/j.med.2019.09.003.
13. Nodule net: A prospective safety net program to reduce loss to follow-up and increase early detection of lung cancer. Harpreet Singh et al. DOI: 10.1200/JCO.2021.39.15_suppl.1564 Journal of Clinical Oncology 39, no. 15_suppl (May 20, 2021) 1564-1564.

SUMMARY OF THE INVENTION

According to the invention there is provided a display system for a computer aided lung image review system comprising: a user interface which comprises: a patient information display wherein the patient information comprises one or more of: patient name, patient age, patient sex, smoking history, disease history, and current patient status; an image display for displaying at least one of a selected plurality of medical images acquired at different times and an associated image report; and a patient timeline display for providing a visual display of patient events over a set time period; and a proxy data store to store the selected plurality of medical images, wherein the selected plurality of medical images are provided from an external archive and are pre-selected to comprise one or more relevant archive images, and exclude irrelevant archive images.

Preferably, the user interface further comprises: a lung cancer risk score display; and a clinical summary display.

In a preferred embodiment of the invention the plurality of medical images are CT images.

Further preferably, the plurality of medical images are sets of image slices around a specific patient location forming image stacks, and the user is able to select images from the image stacks to be provided from the external archive to the proxy data store. Further preferably, the image display prioritizes the download from the proxy data store of those image slices in the proximity of the image location being viewed by the system user.

In an embodiment of the invention, the patient timeline display is reviewed, and patient events that are irrelevant to the lung cancer diagnosis are removed from the timeline display and archived. Further preferably, the irrelevant events are archived either automatically, or manually after review of the patient timeline by a system user.

In a embodiment of the invention, the display system further comprising an analysis circuit for analysing at least one displayed image, to perform at least one of: determining and marking the location of one or more features on the image; determining a lung cancer risk score for one or more of the marked features on the image.

Preferably, the analysis circuit is configured to include manual annotations from a user to mark the location of one or more features on the image.

In a preferred embodiment of the invention, the manual marking of the image feature is done by selecting an image feature in the image display.

In a further preferred embodiment of the invention, the manual marking of the image feature triggers the computation of a disease risk score by the analysis circuit.

Preferably, the marked feature is a lung nodule.

Further preferably, the analysis circuit is further configured to allow a user to navigate directly to a marked location on the image.

In a preferred embodiment of the invention the at least two images are displayed with marked locations, and the analysis circuit synchronises the navigation to the marked location on the at least two images.

Preferably, the analysis circuit enables a system user to edit information about the marked location on the image.

In an embodiment of the invention the patient information timeline can be updated with new information. Further preferably, the patient information timeline is updated manually or automatically.

In an embodiment of the invention, further images are provided from the external archive to update the available images for display.

Preferably, the patient timeline and the image display are linked so that timeline events relative to the displayed image are highlighted on the patient timeline.

Further preferably, user can review archived images, and restore selected archive images to the image display.

Preferably, the lung image review system is a CADx system or a CADe system.

BRIEF DESCRIPTION OF THE FIGURES

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIG. 1 illustrates the system according to an embodiment of the invention;

FIG. 2(a) is an example of a patient information unit that is fully populated according to an embodiment of the invention;

FIG. 2(b) is an example of part of the patient information unit of FIG. 2(a);

FIG. 2(c) shows example patient statuses in the system;

FIG. 3(a) is an example of a timeline information unit according to an embodiment of the invention;

FIG. 3(b) is an example of a timeline information unit for displaying archived information according to an embodiment of the invention;

FIG. 4 shows an example of a medical image and a corresponding report;

FIG. 5 shows example of a medical images acquired at different times;

FIGS. 6(a) and 6(b) show examples of a lung cancer risk score unit and an actions unit, respectively;

FIG. 7(a) shows an example data flow according to an embodiment of the invention;

FIG. 7(b) shows patient page actions and automated status;

DETAILED DESCRIPTION

Overview of the Invention

The invention is a display system for a CADx or CADe system which can display selected medical images from an archive, to allow a reviewer to analyse relevant images, and exclude irrelevant images, thus providing better use of bandwidth for downloading images, as well as more efficient use of the display system.

The system of this invention aims to aid clinicians in making appropriate recommendations for patients with indeterminate pulmonary nodules by providing one or more integrated, interactive functions via one user interface: (1) a computer aided detection (CADe) function to aid clinicians in locating pulmonary nodules in imaging datasets, (2) a computer aided diagnosis (CADx) function to aid clinicians in estimating the risk of identified nodules being malignant, against the risk of invasive procedures for benign nodules, and (3) a tracking function to reduce patient loss to follow-up.

FIG. 1 shows an overview of the display system 100 in this invention. The system has a display 150, a keyboard 152 and mouse 154. The display includes a user interface 102 which preferably consists of six main panels 104, 106, 108, 110, 112, 114, each of which allows the user to consult or interact with a functional unit, via the mouse 154 or keyboard 152. Voice input (not shown) may also be possible as well. In some embodiments of the invention, the system may also comprise an analysis circuit 140. These are described in detail in the rest of this section. The interface 102 is for a single patient. As described, the display system for a computer aided lung cancer diagnosis or detection system comprises a user interface which comprises: a patient information panel wherein the patient information comprises one or more of: patient name, patient age, patient sex, smoking history, disease history, and current patient status; an image display panel for displaying at least one of a selected plurality of medical images acquired at different times and an associated image report; a patient timeline panel for providing a visual display of patient events over a set time period; optionally a lung cancer risk score panel for displaying the results of diagnostic tests; and optionally a clinical decision panel to facilitate and track the process of clinical decision making; a proxy data store to store the selected plurality of medical images, wherein the selected plurality of medical images are provided from an external archive and are pre-selected to comprise one or more relevant archive images, and exclude irrelevant archive images; and an analysis circuit implementing a variety of analysis systems to aid in the diagnosis of lung cancer such as a lung nodule detection system 144 or a malignancy risk scoring system 142. In a preferred embodiment of the invention, further images are provided from the external archive to update the available images for display.

The various panels in the user interface 102 are detailed next:

Panel 1 is a patient information panel 104: an interactive panel displaying and allowing the clinician or other user to edit necessary patient information, including but not limited to information on age, sex, smoking history, cancer history, allowing the clinician or other user to incorporate information relevant to lung cancer into diagnostic follow-up decisions.

Panel 2 is a patient timeline panel 106. This is an interactive panel with a visual representation of a timeline, upon which only relevant events, including imaging studies, can be seen and selected to be viewed in detail. Preferably the imaging studies in the plurality of medical images are CT images, showing all or part of a patient's lung, but other imaging methodologies may also be possible. Preferably, the patient information timeline can be updated with new information. This updating of the patient information timeline can be done either manually or automatically This selective display of imaging studies, visually associated with time, is intended to provide an intuitive history of relevant patient imaging and other events for a patient, without being clouded by studies and events unrelated to lung cancer. In an embodiment of the invention, the patient timeline display is reviewed, and patient events that are irrelevant to a lung cancer diagnosis are removed from the patient timeline display and archived. Preferably, the irrelevant events are archived cither automatically, or manually after review of the patient timeline by a system user.

In some embodiments of the invention, the patient timeline and the image display are linked so that timeline events relative to the displayed image are highlighted on the patient timeline display.

Panel 3 is an image display panel 108, and is an interactive panel to display medical images, particularly CT datasets, with the device's interactive medical image unit, allowing a clinician or other system user to navigate to any position on the medical CT image, view marked or annotated lung nodules on the medical image and mark or annotate lung nodules on the image, preferably the lung nodules will be manually marked on the image. If applicable, the user interface may also include a lung cancer risk score from a CADx component.

Panel 4 is an interactive panel for displaying a report or a CT viewer 110. This panel 110 is alongside (visually associated with) panel 3, image display 108. By the clinician's choice, panel 110 can either display the radiological report associated with the CT image displayed in panel 108, or the latest CT for this patient in a second interactive medical image unit, with a previous one displayed in panel 108. The former enables intuitive association of the image with its report; the latter enables viewing progression of lung nodules over time.

In a preferred embodiment of the invention, the user interface 102 also comprises a lung cancer risk score display; and a clinical summary display.

Panel 5 is an interactive panel 112 displaying information necessary to interpret the lung cancer risk score, that is provided.

Panel 6 is an interactive panel 114 enabling clinicians to take clinical actions such as recommending the next diagnostic step for the patient, or to flag the patient for a colleague or multidisciplinary team meeting. In combining one or more of the panels, these clinical actions are performed in the same context as viewing all relevant information and minimal irrelevant information, with the intention of reducing the clinician's cognitive load, increasing efficiency and reducing the risk of errors, compared to current practices.

Aside from the user interface described above, the system in this invention contains other components depicted in FIG. 1. These are retained in a separate component to facilitate distribution of different parts of the system to different servers:

In some embodiments of the invention, the analysis circuit is configured to include manual annotations from a user to mark the location of one of more features on the image. Preferably, manual marking of the image feature is done by selecting an image feature in the image display. In some cases, the manual marking of the image feature on the displayed image will trigger the computation of a disease risk score by the analysis circuit. In a further embodiment of the invention the analysis circuit is configured to allow a user to navigate directly to a marked location on a displayed medical image. In a preferred embodiment of the system, the analysis circuit contains components, typically based on machine learning models, that provide CADx 142 and CADe 144 functions.

The backend part 120 of the system 100 includes processing logic necessary for processing data flow through the system. This includes a local store 122 of hospital DICOM data, and a database component 124 for persistent storage of relevant patient data. The backend 120 connects to external hospital servers 130, 132 to obtain necessary image and report data.

The functionality in each of the panels in the user interface of this invention is powered by a functional unit, each of which is described next:

Patient Information Unit 200, 220

The user interface 102 includes patient identification and other pertinent information about the patient. This is provided by this unit, displayed in Panel 104.

FIG. 2(*a*) shows the full patient information unit 200.

FIG. 2(*b*) shows the essential information only 220, which may be displayed in the panel 104, for example when the user scrolls the user interface, taking up less room while retaining the essential information in view. Essential information is typically name 222, sex 226, date of birth 224, and as described in following paragraphs, patient status 230 and a link to view the patient's history log 236.

From left to right in FIG. 2(*a*), the unit contains:

Active elements to allow the clinician to view the previous or next patient on a list 201.

Essential patient identification information: patient name 202/222, date of birth 204/224, sex 206/226 and patient's hospital identification code 208/228. The patient information unit includes further information as discussed below.

The patient's nodule clinic status, e.g. "Missed a follow-up" or "Awaiting clinical review" is shown at 210/230. Indication of this status 210/230 is optionally colour-coded for urgency. For example: "Missed a follow-up" is red (this means a patient was scheduled for a follow-up scan, but an imaging study is not available around the planned date of the follow-up); "Awaiting clinical review" is amber (there is a new imaging study available and the patient awaits a follow-up decision from a clinician); "Flagged . . . " is amber (the case has been flagged for either the managing clinician or multidisciplinary team meeting, or so-called tumour board for discussion of the pending decision on the next step); "Follow-up scheduled" is green (a follow-up has been scheduled for a future date, therefore no action for this patient is required). These different possible status updates are shown in FIG. 2(*c*). This status is preferably set automatically by the system 100 in reaction to certain events (see FIG. 7(*b*) as described in more detail later in the description), allows straightforward filtering of a list of patients (not part of this invention) to reduce patient management related risks such as loss to follow-up.

FIG. 2(*a*) also shows relevant patient history 212, including smoking history, cancer history, managing clinician and general notes. The system 100 provides the ability for a clinician or other user to update this information, via link 214.

The display system also has the ability for the clinician to view the history of one or more actions taken within the patient's journey through the nodule clinic, for example, the history of follow-up decisions taken, via link 216/236.

The full patient information unit 200 has the ability for the clinician to refresh the system's available imaging studies from a connected hospital PACS, via link 217.

Finally, the full patient information unit 200 has the ability for the clinician to obtain a self-contained report containing information pertinent to lung cancer diagnosis for the patient, via link 218.

Data for this unit is obtained by the backend 120, initially from DICOM header data from the connected hospital PACS 130 (patient's identification data) and entered by the user (smoking and cancer history). In both cases, data is persisted in the system's own data store 124, which is used as the source of this data once the patient is enrolled into the system.

Event Timeline Unit

Figure 3A:
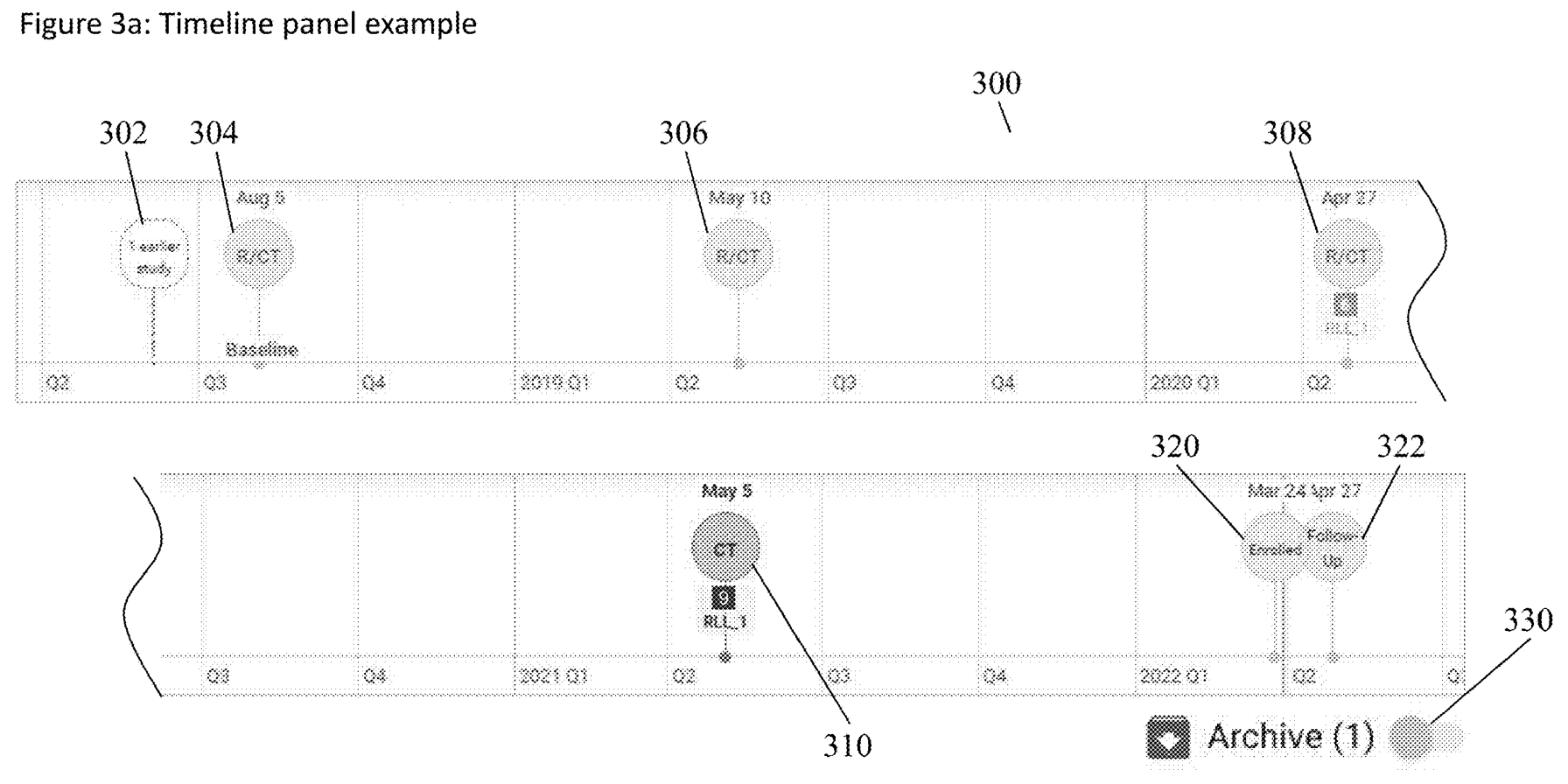

The timeline unit 300 (FIGS. 3(*a*) and 3(*b*)), displayed in Panel 106, has been designed to allow the clinician, with minimal cognitive load, to quickly establish an overview of the clinical events associated with the displayed patient. FIG. 3(*a*) shows an example timeline unit, and FIG. 3(*b*) shows an example timeline unit including details from an archived study. As shown, the timeline is divided into years, and each year is divided into quarters. Relevant events are then shown in the specific quarter when the event occurred. For example, FIG. 3(*a*) shows one earlier study prior to Q3 of 2018, 302, this is followed by a baseline CT scan at 304 in Q3 of 2018 (Aug 5). The next event is a CT scan in Q2 of 2019 (May 10) 306, then on Apr 27 in Q2 of 2020 there is another CT scan, 308, this is followed by a CT scan on May 5 (Q2) of 2021 310. Finally on FIG. 3(*a*) is shown an enrolment appointment on Mar 24 (Q1) of 2022 at 320, and a follow up appointment on Apr 27 (Q2) of 2022, 322. FIG. 3(*b*) is similar but also shows an archived study 332, that occurred on Feb 3 (Q1) of 2021.

As shown in FIGS. 3(*a*) and (*b*) while displaying the record of a patient who has been enrolled in the nodule clinic for several years due to annual follow-ups, the events such the baseline CT scan, enrolment in the clinic and follow-up scan history can quickly be ascertained and displayed. Each CT imaging study is represented by a visual element, which, when selected, displays the image study and any associated report in the other panels, and the fact that it has been selected is represented by visual cues such as colour and font weight of the element 310 in the timeline.

The invention includes a method of marking a particular CT imaging study as the baseline study for the purpose of the lung nodule clinic. In this embodiment of the invention the scan of Aug. 5, 2018, 304 is the baseline study. From this study onwards, changes in lung nodule appearance over time can be judged. This is indicated on the timeline display, and studies prior to the baseline are automatically archived, thereby removing irrelevant information from the immediate view of the clinician). This view is further enhanced because the timeline's full width is used to represent the timeframe relevant for the patient's lung nodule follow-up. One or more earlier studies 302 are displayed as a dotted outline on the far left of the display, and the baseline study 304 is marked as such on the timeline (see FIG. 3).

Some patients, especially those where a lung nodule was detected incidentally, may have many imaging studies not useful for assessment of lung nodules, for example in the case of a broken limb. Therefore, the invention includes a method to automatically archive imaging studies that are not relevant to the lung nodule clinic. In some examples of the invention, this may be based on a configurable filter on the study's description. In another example, a method is provided for the clinician to archive studies manually. In either case, this allows the clinician to focus only on events relevant to the lung nodule clinic. The timeline allows the clinician to optionally view archived studies and images and if necessary, restore them to the view in the image display, for example as image 332 on FIG. 3(*b*).

Where a CT study has one or more nodules marked or annotated that has resulted in a CADx lung cancer risk score, the highest scoring nodule's name and score are displayed with the representation of that study in the timeline. See FIG. 3(*a*), where the nodule RLL_1, has lung cancer risk scores 6 in image indicated at 308 and a score of 9 for the image indicated at 310, that is a different score at different image acquisition times.

The timeline unit 300, displayed in UI panel 106, also displays events pertinent to the nodule clinic, date of enrolment 320, and the date the next follow-up 322, is due. This, together with the displayed patient status (in the patient information unit 210/230) helps the clinician keep track of lung nodule patients, to reduce the risk that they are lost to follow-up.

Data for this unit is obtained by the backend 120, and processed accordingly (see FIG. 7(*a*)):

When the patient is seen by the system for the first time, the backend 120 pulls relevant images from the hospital PACS 130 and stores them in the system's PACS proxy data store 122. This serves two main purposes: firstly, the local storage of images used in the system reduces burden on the hospital PACS 130 and makes loading its slices to the user interface on demand more efficient; secondly, the backend 120 retrieves only image types relevant to the system, i.e. CT images, reducing the potential for users needing to search through many irrelevant images.

System-specific attributes for each image are stored in the system's patient clinical database 124 (e.g. the images' dates, archive status). This has the benefits of not needing to access the image data itself to build the patient timeline and allowing archived images to be marked as such here, while a large amount of unnecessary image data is removed from the system's PACS proxy, saving storage space.

For patients already in the system, the backend 120 periodically checks for new CT images appearing in the hospital PACS 130. Timing is configured at the system level, for example once per day, pulling any CT images from the hospital PACS 130 that are not already present in the system's own databases 122/124. This process can also be initiated immediately by a user for a single patient (217, see Actions unit).

Archiving of CT studies from the timeline: patients in the system may have many imaging studies, a large proportion of which may be irrelevant for lung nodule diagnosis. While filtering for CT scans partly addresses removing irrelevant scans from the default view of the timeline, this is further enhanced by giving the user the ability to archive (hide from the timeline) irrelevant CT scans. This also has the benefit of removing the image data from the system's PACS proxy storage 122 (the system never modifies or deletes data in hospital PACS 130). On viewing an image that is irrelevant, the user can select to archive it (the control for this function is in the interactive medical image unit). On receiving this request, the backend marks the imaging study as archived in the system's patient clinical database, and the user interface for the timeline updated to hide it. The image data for the study is deleted in a batch process run periodically, for example overnight.

Figure 3B:
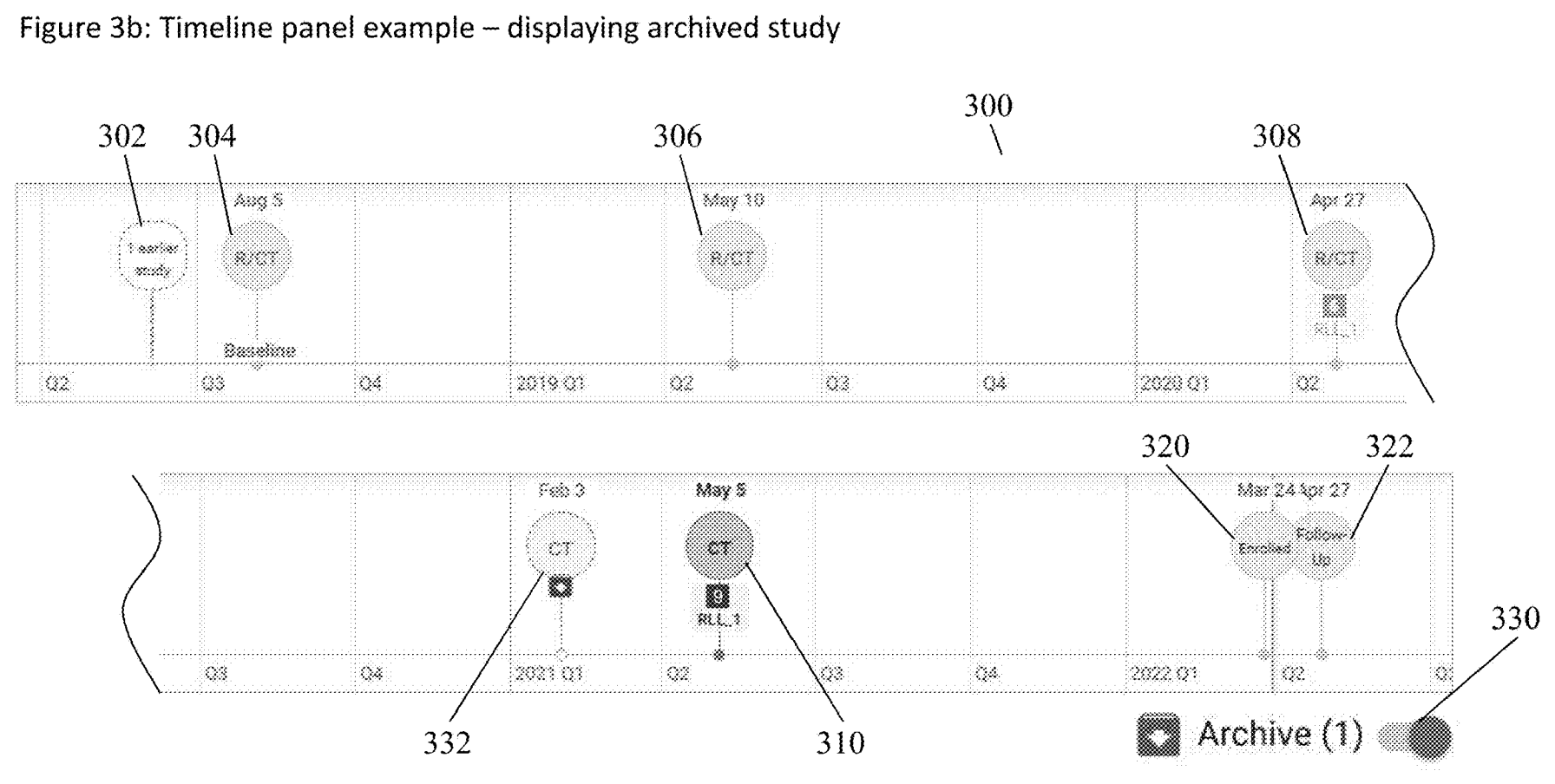

Viewing archived studies on the timeline: the default view of the timeline is with archived studies hidden (see FIG. 3(a)). A control 330 in the user interface of the timeline indicates the number of archived images for this patient and provides a binary control to show them. On selecting this control, the user sees the archived studies in the timeline, visually distinguished from non-archived studies by a dotted outline 332 (FIG. 3(b)). Once the image data has been deleted from the system's PACS proxy, the indication in the timeline is both dotted outline and greyed out.

Viewing archived images (not yet deleted from PACS proxy): the user selects to view archived studies on the timeline and uses the mouse to click the indication of this study in the timeline. The image is then viewed in the interactive medical image unit in Panel 3, 108.

Viewing archived images (deleted from PACS proxy 122): the user selects 330 to view archived studies on the timeline and uses the mouse 154 to click the indication of this study in the timeline. The interactive medical image unit in Panel 3, 108 then displays text to inform the user that the image needs to be downloaded from the hospital PACS, and a user interface element to allow the user to initiate this action. On selecting this element with the mouse button, the backend uses the image's DICOM identification data (stored in the system's patient clinical database 124) to retrieve the image data to the system's PACS proxy store and displays it in the interactive medical unit in Panel 3, 180.

Restoring archived images: archived studies displayed as described above can be restored (un-archived), by the user selecting a control in the interactive medical image unit, which causes the backend to update the image's status in the system's patient clinical database to non-archived, so next time the timeline default view is displayed (without archived studies shown), the restored study is indicated on the timeline.

Interactive Medical Image Unit 400/500

The interactive medical image unit 400/500 is present in Panel 3, 108, and, when the clinician has selected to do so, in Panel 4, 110, so that two images can be displayed side by side, as shown in FIG. 5. Panel 3, 108, can contain any of the medical images 402/502 selected in the timeline, while Panel 4, 110, contains either a report 450, preferably a radiology report, or an image from the latest imaging study 504, as in FIG. 5.

Data used by this unit is managed by the backend 120, which obtains new DICOM image data from the hospital's PACS 130. To view the image data in the system the backend 120 stores the data in the system's own PACS proxy database 122, allowing for subsequent efficiency in displaying the data without further burdening the hospital PACS 130, and facilitating fast download of image slices as needed in the user interface.

The medical image unit includes:

Study selector 406: should there be two or more imaging studies on the same day, the unit includes a selector, which allows the clinician to select a single study. This selector may automatically select the most recently selected study or the study most likely to be relevant to lung cancer diagnosis, for example by the study's description. (Note that in DICOM, a single study contains one or more series, and a single medical image dataset is contained in one series.)

Series selector 408: for studies with more than one series, this selector allows the clinician to select a single dataset to view and interact with. For series that are suitable for assessment by the CADx lung cancer risk score component, this is indicated, for example with an identifiable logo 410 next to the series description in the selector. When the study is displayed, the series selector may automatically select the most recently selected series or the series most likely to be relevant to lung cancer diagnosis, for example by the series' description. The user selecting a series in the user interface instructs the backend 120 of the system to retrieve information associated with the image from the patient clinical database, and if available, image data from the system's PACS proxy 122. Both are transferred to the system's user interface for user interaction.

A study-level selector 412, which allows the clinician to (1) set the selected study as the baseline study for the purpose of the nodule clinic, and (2) select to archive the study, so it is not shown by default in the timeline. (1) allows the clinician to focus on the progress of the patient's lung nodules from the time one first appeared on a scan, without viewing previous irrelevant studies. (2) allows the clinician to archive (hide from the timeline) any other studies that are not relevant to lung cancer (see timeline unit section for further details). The user selecting a study in the user interface instructs the backend 120 of the system to retrieve information associated with the study, including its images, from the patient clinical database 124, and if available, image data from the system's PACS proxy 122. Both are transferred to the system's user interface for user interaction. As an additional automated step, the system selects a series within the study that is most likely to be useful to the user. For example, this may be by selecting the series previously selected for this study, or the one where nodules are already marked or annotated.

An indication 414 of the marked or annotated nodules in the selected study, by name, and if there is one, the CADx malignancy risk score for each one 416. When the clinician selects a nodule here, the system automatically scrolls to the CT slice on which the nodule is marked. If the user has selected to display a medical image unit 400/500 in Panel 110, as in FIG. 5, and that image has a marked nodule of the same name, the system automatically scrolls to the CT slice on which the nodule is marked. This has the intention of shortening the time taken for the clinician to assess the nodule's progress over time.

Series level controls 418, 420, 422 for the clinician to edit nodule marking or annotation on the selected series: add, edit, delete. The system allows the clinician to add a new mark 430 for a solid, part-solid, GGO (ground glass opacity) or other type of nodule, or to mark a nodule previously marked on other studies; to edit the location of an existing nodule mark; or to delete a nodule mark. Adding a nodule mark may be achieved by the clinician indicating only the centre of the nodule on the CT image.

Adding a new nodule mark or annotation: the system provides a control 418 in the user interface to add a named nodule to the image. The name is selected first, from a pre-defined list of names designed to indicate which lung and which lobe the nodule is located. Once the name is selected, the user interface allows the user to scroll to the slice estimated by the user to contain the centroid of a lung nodule. On using the mouse to indicate the location of the centroid, the three-dimensional location of the click point is sent to the backend of the system. The backend stores the location of the click point and the nodule's name, along with the series identification, in the system's patient clinical database

124. If the attributes of the image are appropriate for CADx scoring, the backend 120 creates a dataset containing pixel information around the location of the click point, and sends this dataset, via a network connection to the CADx malignancy risk score service 142 in the analysis circuit 140. The malignancy risk score service uses the data to provide a malignancy risk score, which is sent back to the backend, saved in the system's patient clinical database 124 and sent to the user interface to be displayed to the user 432.

Editing the location of an existing nodule mark or annotation: the system provides a control 420 in the user interface to select a new three-dimensional location for a nodule mark already existing on the image. The new location is obtained and processed by the system in the same way as described for adding a new nodule.

Deleting an existing nodule mark or annotation: the system provides a control 422 in the user interface to remove the mark of an existing nodule mark. The user selects the name of the marked nodule, confirms, then the backend 120 of the system removes the mark and any associated score from the system's patient clinical database 124.

A series level control 424 for initiating automatic detection of nodules on the image (CADe), which prompts the clinician to view and optionally confirm the correctness of each nodule detection. This has the intention of making detection of nodules more efficient and making it less likely for nodules to be missed.

On initiation of the nodule detection by the user, the system takes all CT image data and sends it through a network connection to the nodule detection service 144 in the analysis circuit 140. The nodule detection service returns to the backend the three-dimensional locations of marks indicating potential nodules it finds, as in 430, but identifiable by the user as an automatically-detected (unconfirmed) nodule. The backend saves them in the patient clinical database as unconfirmed nodule marks. If the image is still displayed in the user interface, the system displays these locations on the CT image.

To confirm a detected potential nodule, the user selects a control in the system's user interface, selecting a name from a pre-defined list of names, and the backend of the system saves this to the system's patient clinical database.

To remove a detected potential nodule, the user selects a control in the system's user interface and the backend deletes the mark from the system's patient clinical database.

An interactive view of a single CT dataset, enabling the clinician to scroll through slices of the dataset, along with standard medical image viewing features such as zoom, pan, adjustment of Window Levels 426, the ability to reset these to system defaults 427, and to optionally hide marked nodules from the display 428.

For the image display 402, the slices immediately around the current location are downloaded for viewing, but the entire image stack is not. This prevents unnecessary use of network bandwidth between the user interface and the system's PACS proxy database, preventing downloads of data that is not viewed by the clinician. In a preferred embodiment of the invention, the plurality of medical images are sets of image slices preferably around a specific patient location forming one or more image stacks, and the user is able to select images from the one or more image stacks to be provided from the external archive to the proxy data store. In an embodiment of the invention the image display prioritizes the download from the proxy data store of those image slices in the proximity of the image location being viewed by the system user.

As the clinician navigates the slice stack, nearby slices are downloaded. The progress of slice downloading is displayed 434 at the image display: the entire stack is represented, for instance, with green areas indicating downloaded slices, orange areas indicating slices currently being downloaded, and red areas indicating non-downloaded slices (see FIG. 4), providing visual cues to the user about download progress. This indicator also displays the relative slice location of marked lung nodules 436 and allows the clinician to select any slice location directly here, or to select a particular nodule to view. Both features offer a shortcut to a particular location in the dataset's slice stack.

Radiology Report Unit

Panel 4, 110, can contain the radiology report unit 450, which displays the radiologist report of the imaging study displayed in Panel 3, 108. This may be a simple display of an existing report but is important that the report is available to the clinician at the same time as viewing the medical image to which the report relates. The report provides important information that is considered before the clinician's decision about the next diagnostic step.

The backend 120 of the system automatically obtains the correct report from the hospital's reporting system 132. The correct report is identified by matching the accession number in the image's DICOM header to the accession number for the report. This means that the report that is uniquely associated with the image displayed in Panel 108 is the only report that can be displayed adjacent to it.

Selection of Report/Latest Image

The system 100 includes an element 440/540 to select between two views: a medical image dataset and the associated report (the "Report with CT" configuration), that is an image displayed in panel 108, with a report in panel 110 and the latest medical image dataset with a selected previous one (the "Compare with latest CT" configuration), that is an image displayed in 108, and a second image displayed in panel 110. Selecting to view the report instructs the backend 120 to retrieve the correct report, which is displayed in the user interface 102, in panel 4, 110, as described above.

When two images are displayed (see FIG. 5):

when the clinician selects to view a nodule in one image dataset (in panel 108 or 110), if the nodule is marked in the image that is being displayed in the other panel, the system 100 automatically displays the image slice on which the same nodule is marked in the other panel: a single user action results in the same nodule being displayed in both images.

when the clinician interactively changes the image display (e.g., Window/Level), both images' display is updated simultaneously.

the view configuration includes an indication of the time between the images shown 530, which is calculated by the system from the dates of the two images, included in the images' DICOM headers.

Lung Cancer Risk Score Unit

The lung cancer risk score unit, displayed in Panel 5, 112 (see FIG. 6(*a*)), contains elements that allow the clinician to:

Correctly interpret the lung cancer risk score. For example, this may take the form of a histogram 602 display depicting all possible scores 604, and the proportion 606, in a patient population with known ground truth nodule malignancy, of benign against malignant nodules for each score. This would be the only way the score should be interpreted for clinical use of the invention.

Actions Unit

The actions unit, displayed in Panel 6, 114 (see FIG. 6(*b*)), contains elements that allow the clinician to:

Where a patient is awaiting clinical review, flag the patient for either the patient's managing clinician 652 or a multidisciplinary team (sometimes referred to as a tumour board), 654. Flagging of the patient, initiated by the user via the user interface 102, is stored by the backend 120 into the system's own patient clinical database 124.

Mark the patient as discharged from the nodule clinic 656. This would typically happen where a patient has no malignant lung nodule, in the event of patient death, or if the clinic otherwise deems the patient lost to follow-up. This marks the status of the patient as Discharged, and the patient is no longer tracked in the system.

Mark the patient as referred, for example to a lung cancer treatment team after a positive diagnosis is confirmed 658. This marks the status of the patient as Referred, and the patient is no longer tracked in the system.

For a patient still in the nodule clinic and awaiting clinical review, the clinician can record their recommendation for the next diagnosis step for this patient, for example a 12-month follow-up CT scan or a biopsy, using control 660. The system automatically updates the patient's status to "Follow-up scheduled".

For a patient whose status is "Missed a follow-up", the system provides a different list of next action decisions, namely to re-schedule the follow-up for this patient, also using control 660. This reverts the patient status to "Follow-up scheduled".

For a patient whose follow-up is scheduled, enter the date of the expected follow-up. When this date passes (with configurable tolerance), the system automatically updates the patient's status to "Missed a follow-up", enabling clinical staff to investigate, with the aim of reducing the patient's probability of loss to follow-up.

For a patient who may have a new imaging study available in the hospital PACS 130, but this has not yet been retrieved by the system, the user is provided with a control in the Actions unit, which when mouse-clicked, instructs the system to perform the image study synchronisation for this patient (sec Event timeline unit section). Preferably, at least two images are displayed with marked locations, and the analysis circuit synchronises the navigation to the marked location on the at least two images.

All status updates initiated by the user as described above are achieved by the system's backend 120 setting the patient's status within the system's patient clinical database.

Analysis Circuit

In a preferred embodiment of this invention, the system 100 to aid clinicians in the diagnosis of indeterminate lung nodules, is further supported by an analysis circuit 140. The analysis circuit 140 provides automated functionalities that compute information relevant to the lung cancer diagnosis of the patient being examined.

An example of the analysis circuit 140 include a unit 142 to compute the risk of malignancy of lung nodules. This computation may be triggered, for example, through the marking or annotation of a lung nodule in the medical image in Panel 3, 108. Preferably, the analysis circuit for analysing at least one displayed image is configure to perform at least one of: determining and marking the location of one or more features on the image; determining a lung cancer risk score for one or more of the marked features on the image. In an embodiment of the invention, the analysis circuit is configured to include one or more manual annotations from a user to manually mark the location of one of more features on the image. Preferably, the manual marking of the image feature is done by selecting an image feature in the image display. In a further embodiment of the invention, the manual marking of the image feature is done by selecting an image feature in the image display. In a preferred embodiment of the invention the manual marking of the image feature triggers the computation of a disease risk score by the analysis circuit. Preferably, the analysis circuit is further configured to allow a user to navigate directly to a marked location on the image. Preferably, the analysis circuit enables a system user to edit information about one or more marked locations on the image.

The result of a malignancy risk computation by the analysis circuit is then presented to the user in Panel 5, 112. In other examples of this invention, further nodule characterization units can operate alongside the malignancy risk scoring. For example, a characterization of the invasiveness or invasiveness potential of the lung nodule, or a prediction of a histological subtype.

Another example of the analysis circuit 140 includes a unit for the automated detection of lung nodules 144 from the medical image. For example, this can be triggered from the series-level control 424 in Panel 3, 108. This unit inspects the CT image looking for lung nodules and returns the location of likely lung nodules. CADx functionalities such as malignancy risk prediction are also computed on the lung nodules automatically identified by the lung nodule detection unit.

Another example of the analysis circuit 140 includes the automated computation of patient-level characteristics that may be associated with lung cancer. For example, the identification and marking of emphysema as well as other types of relevant lung damage such as lung fibrosis.

Data Flow Overview (FIG. 7(*a*))

Image data from the hospital PACS system 130 is brought into the system's PACS proxy 122 by two mechanisms. First, a batch process 702 configured to run at regular intervals, which for only enrolled patients 710, queries the hospital PACS for CT studies 706 not archived 708 by the system and transfers any new data to the system's PACS proxy 122. Second, for a patient displayed in the user interface 102, a user may initiate 704 the same process for this patient only 712.

The user interface 102 displays: image data from the PACS proxy in its medical image unit(s) 400/500, obtaining only the currently displayed image slice and those close to it 712; and where the user has selected to view a patient report with a single image (as in FIG. 4), the system obtains 714 any report with the same accession number as the image, from hospital system 132.

Automated Status Setting in the System (FIG. 7(*b*))

Various automated patient status changes occur in the system, triggered by different events. Patient statuses are listed in the patient information unit section and depicted in FIG. 2(*c*), and stored in the system's database 124. FIG. 7(*b*) summarises these automations:

If the patient displayed in the user interface 102 has status "Missed follow-up" 730, if the follow-up has been completed, the user optionally syncs the system's medical images with the hospital PACS (704), then the system 100 updates the patient's status to "Awaiting clinical review" 754. If the patient's follow-up has not been completed, the user can optionally re-schedule the follow-up, in which case the system updates the patient's status to "Follow-up scheduled" 756, or mark the patient as status as discharged (e.g. died or lost to follow-up), in which case the system 100 updates the patient's status to "Discharged" 758.

If the patient has status "Awaiting clinical review" or "Flagged . . . ", the user has several options: the patient can be marked as referred, for example in the case of a positive diagnosis for cancer, in which case the system 100 updates the patient status to "Referred" 760; the patient can be marked as discharged, for example if the patient has a confirmed negative diagnosis, in which case the system updates the patient's status to "Discharged" 762; the user can enter a follow-up decision into the system (see action unit, FIG. 6(*b*), 660), in which case the system updates the patient's status to "Follow-up scheduled" 764; the patient can be flagged (see actions unit, FIG. 6(*b*), 652/654), in which case the system updates the patient's status to, for example, "Flagged to managing clinician" or "Flagged to tumour board" 766. Additionally, FIG. 7(*b*) depicts the process of the user marking a nodule 770 and the system generating the lung cancer risk score 772.

If the patient has status "Discharged" or "Referred" 738, the patient can optionally be re-enrolled to the nodule clinic, in which case, the system updates the patient's status to "Awaiting clinical review".

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for automated contouring of cone-beam CT images.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media (e.g., CD ROM, CD R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A display system for a computer aided lung image review system comprising:

a user interface which comprises:

a patient information display wherein the patient information comprises one or more of: patient name, patient age, patient sex, smoking history, disease history, and current patient status;

an image display for displaying at least one of a selected plurality of medical images acquired at different times and an associated image report; and a patient timeline display for providing a visual display of patient events over a set time period;

a proxy data store to store the selected plurality of medical images;

an analysis circuit for analysing at least one displayed image, to perform at least one of: determining and marking the location of one or more features on the image; determining a lung cancer risk score for one or more of the marked features on the image, where the analysis circuit is configured to include one or more manual annotations from a user to manually mark the location of one of more features on the image, wherein the manual marking of the image feature is done by selecting an image feature in the image display, wherein the manual marking of the image feature triggers the computation of a disease risk score by the analysis circuit; and wherein the selected plurality of medical images are provided from an external archive and are pre-selected to comprise one or more relevant archive images, and exclude irrelevant archive images.

2. A display system as claimed in claim 1, wherein the user interface further comprises:

a lung cancer risk score display; and a clinical summary display.

3. A display system as claimed in claim 1, wherein the plurality of medical images are CT images.

4. A display system as claimed in claim 3, wherein the plurality of medical images are sets of image slices forming one or more image stacks, and a user is able to select images from the image stacks to be provided from the external archive to the proxy data store.

5. A display system as claimed in claim 4, wherein the image display prioritizes the download from the proxy data store of those image slices in the proximity of the image location being viewed by the system user.

6. A display system as claimed in claim 1, wherein the patient timeline display is reviewed, and patient events that are irrelevant to a lung cancer diagnosis are removed from the patient timeline display and archived.

7. A display system as claimed in claim 6, wherein the irrelevant events are archived either automatically, or manually after review of the patient timeline by a system user.

8. A display system as claimed in claim 7, wherein a study in the patient timeline display can be marked as the baseline study of a patient.

9. A display system as claimed in claim 1, wherein the marked feature is a lung nodule.

10. A display system as claimed in claim 1, wherein the analysis circuit is further configured to allow a user to navigate directly to a marked location on the image.

11. A display system as claimed in claim 10, wherein at least two images are displayed with marked locations, and the analysis circuit synchronises the navigation to the marked location on the at least two images.

12. A display system as claimed in claim 10, wherein the analysis circuit enables a system user to edit information about the marked location on the image.

13. A display system as claimed in claim 1, wherein the patient information timeline can be updated with new information.

14. A display system as claimed in claim 13, wherein the patient information timeline is updated manually or automatically.

15. A display system as claimed in claim 1, wherein further images are provided from the external archive to update the available images for display.

16. A display system as claimed in claim 1, wherein the patient timeline and the image display are linked so that timeline events relative to the displayed image are highlighted on the patient timeline display.

* * * * *